United States Patent [19]

Hughes

[11] Patent Number: 5,754,622
[45] Date of Patent: May 19, 1998

[54] SYSTEM AND METHOD FOR VERIFYING THE AMOUNT OF RADIATION DELIVERED TO AN OBJECT

[75] Inventor: John H. Hughes, Martinez, Calif.

[73] Assignee: Siemens Medical Systems, Inc., Iselin, N.J.

[21] Appl. No.: 642,065

[22] Filed: May 3, 1996

Related U.S. Application Data

[63] Continuation-in-part of Ser. No. 504,722, Jul. 20, 1995, Pat. No. 5,621,779.
[51] Int. Cl.$^6$ ........................................... G21K 5/10
[52] U.S. Cl. .................. 378/65; 378/64; 378/108; 378/117
[58] Field of Search .......................... 378/65, 64, 108, 378/116, 110, 112, 207, 97, 117

[56] References Cited

U.S. PATENT DOCUMENTS

| | | | |
|---|---|---|---|
| 4,365,341 | 12/1982 | Lam | 378/65 |
| 5,138,647 | 8/1992 | Nguyen et al. | 378/189 |
| 5,511,549 | 4/1996 | Legg et al. | 128/653.1 |
| 5,623,139 | 4/1997 | Sliski | 250/205 |

*Primary Examiner*—Don Wong
*Attorney, Agent, or Firm*—Heather S. Vance

[57] ABSTRACT

Radiation delivered to an object (13) is gathered by a detector unit (91). A central processing unit (18) reverse calculates the radiation delivered by using attenuation factors of the object (13) and exit radiation signals (92) generated by the detector unit (91). The delivered radiation is displayed on the screen of a monitor (70). Simultaneously, a radiation map from a planning system can be displayed. Thus, the amount of radiation delivered to object (13) is measured and can then be verified and displayed. A portal imaging system (90) can contain detector unit (91).

15 Claims, 5 Drawing Sheets

SYSTEM AND METHOD FOR VERIFYING THE AMOUNT OF RADIATION DELIVERED TO AN OBJECT

CROSS REFERENCE TO RELATED APPLICATION

This application is a continuation-in-part of U.S. patent application Ser. No. 08/504,722, filed Jul. 20, 1995, now U.S. Pat. No. 5,621,779, which is incorporated herein by reference in its entirety for all purposes.

BACKGROUND OF THE INVENTION

1. Technical Field

This invention relates to verifying the radiation delivered to an object, and more particularly to a system and a method for measuring the radiation delivered to an object by a radiation treatment device, and then verifying and displaying the delivered radiation.

2. Description of the Related Art

Radiation-emitting devices are generally known and used, for instance, as radiation therapy devices for the treatment of patients. A radiation therapy device generally comprises a gantry which can be swiveled around a horizontal axis of rotation during the course of therapeutic treatment. A linear accelerator is located in the gantry for generating high-energy radiation beam (typically, of electrons or photons, that is, X-rays) for therapy. During treatment, this radiation beam is trained on a zone of a patient lying in the isocenter of the gantry rotation. Radiation treatment devices have built in safety schemes that give the user confidence that the correct radiation is being delivered. However, it is hard to guarantee the delivery of radiation to the treatment site.

Before treatment, an object (e.g., a patient) may be scanned with a computer tomograph (CT), and/or treatment may be simulated with a diagnostic X-ray unit (i.e., a simulator). These devices identify the area in the body to be irradiated and the surrounding critical organs. The physician determines a method of treatment based on the patient's weight and age, along with the type and size of the diseased area. Data from the CT and/or the simulator along with the radiation emitting device data are used in the treatment planning process to calculate the dose levels which are to be delivered to the treatment site. The treatment plan also calculates the radiation exposure to healthy tissue. The physician approves the plan, which is then transferred to the radiation emitting device.

To control the radiation emitted toward an object/patient, an aperture plate arrangement is usually provided in the trajectory of the radiation beam between the radiation source and the object. This aperture plate arrangement defines a field on the patient to which the prescribed radiation is to be delivered. A wedge-shaped radiation distribution can be achieved by introducing, for example, a wedge-shaped absorption filter or a virtual wedge comprising aperture plates which are moving during the irradiation. Such devices, however, modify the actual radiation delivered to the object in a predicted manner. Unfortunately, these devices have no way of determining how much radiation has been deposited to the object because the object may be in a wrong position. Thus, radiation deposited to the object cannot be determined.

U.S. patent application Ser. No. 08/504,722, filed Jul. 20, 1995, describes a system and a method for delivering and displaying radiation delivered to a predetermined field on an object. The accumulated dose delivered to this field is displayed and updated throughout the delivery of radiation. A prescribed dose profile may also be displayed simultaneously so the user can compare the delivered dose with the prescribed dose profile. The delivered dose is sensed and measured by a measuring or dose chamber or by a beam view device located beneath the patient. Dose profiles—both prescribed and delivered—are preferably stored in a memory unit. Profiles for several different areas to be irradiated at several different times may be stored and used to direct and monitor the course of radiation treatment. The profiles can also be reconstructed to product a three dimensional table of the radiation being delivered to the object.

U.S. Pat. No. 5,138,647 describes a portal imaging device in which an image converter plate is arranged beneath the object. The plate converts an image represented by the radiation beam into a visible image. A reflector directs the visible image to a video camera. Such an imaging device allows the user the ability to view the anatomy of the patient during radiation, but it does not give the user any idea of the quantity of radiation being delivered either to the diseased area or to the critical surrounding organs and tissue. The portal imaging device assists the user in verifying that the patient is correctly positioned during the radiation treatment. Should the patient move or be incorrectly positioned, the treatment can be stopped and the patient will be repositioned manually.

During dynamic conformal treatments, the gantry, collimator, jaws and/or multileaf collimators could all be in motion during the radiation treatment. When this occurs, it is even more difficult to verify whether the correct amount of radiation has been delivered to the treatment site because the treatment site lacks monitoring capability. The accelerator's dynamic motions have an impact on the amount of radiation delivered to the object. This impact can be predicted, but cannot be measured because of the objects possible movement.

Each day, when the treatment is delivered, the machine setup and dose values are recorded, either manually or automatically. However, the actual amount of radiation inside the patient is unknown. In light of this, there is a need for verification and display of the amount of radiation received by the object to ensure that the predicted radiation is delivered to the field on the object to be treated.

SUMMARY OF THE INVENTION

According to the invention, a system is provided for verifying the radiation delivered to an object. In one embodiment of the present invention, a radiation source provides an output beam directed to the object. A detector means senses the radiation output from the output beam and generates exit radiation signals. The detector means senses the output radiation from beneath the object. A processing means then calculates the radiation delivered to the object. This processing means uses the exit radiation signals from the detector means for the calculation. In another embodiment of the present invention, an initial output beam of radiation is generated from a radiation source. This initial output beam is directed toward a field to be irradiated on the object. Radiation from the initial output beam is sensed after the radiation passes through the object. A derived output beam is then calculated. This derived output beam is at least in part based on the sensed radiation.

DETAILED DESCRIPTION

The invention is described below with primary reference to a system for delivering X-ray radiation to a patient, and for delimiting the radiation using at least one movable plate located in the beam path from a radiation source. The invention may be used to display the actual delivery of any type of energy, for example, electrons (instead of X-rays) to any type of object (i.e., not just a human patient) provided the amount of radiation passing through the object can be sensed.

Figure 1:
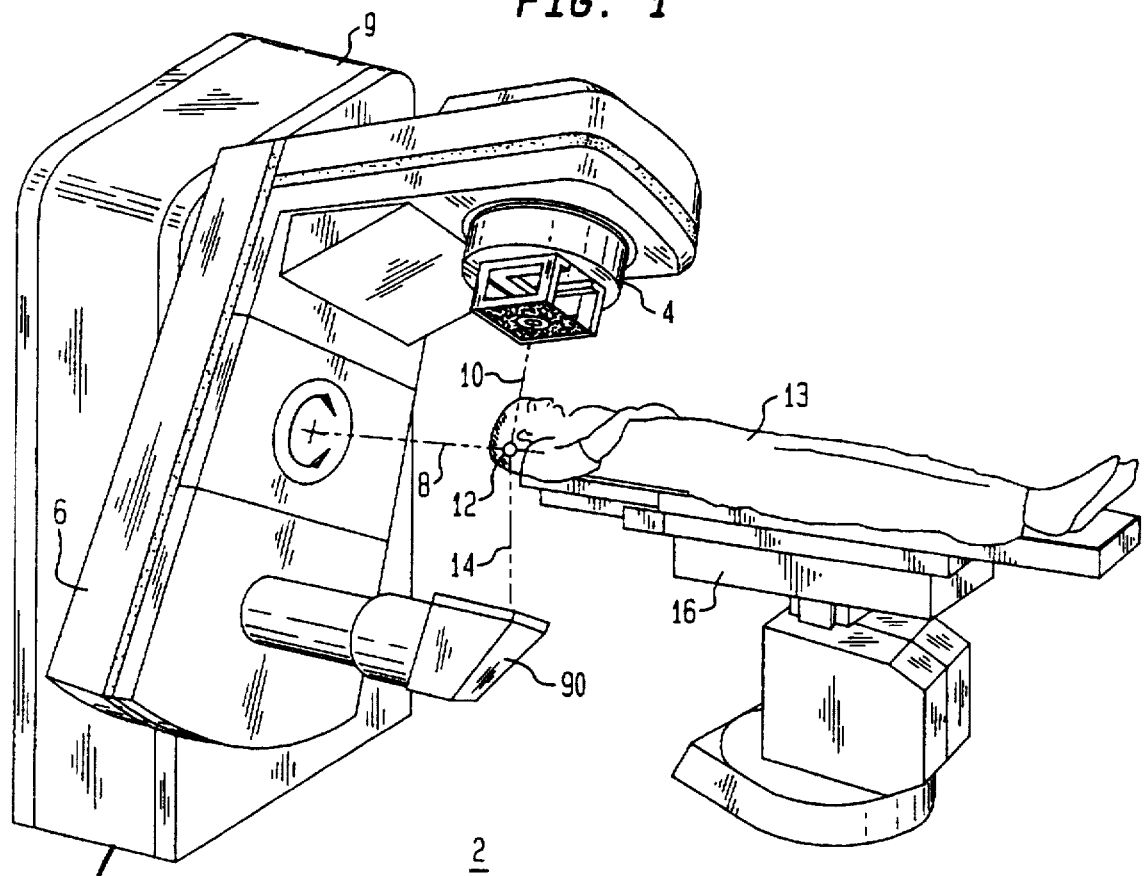
FIG. 1 shows a diagram of a radiation treatment device including a treatment console constructed in accordance with the invention.
Figure 1:
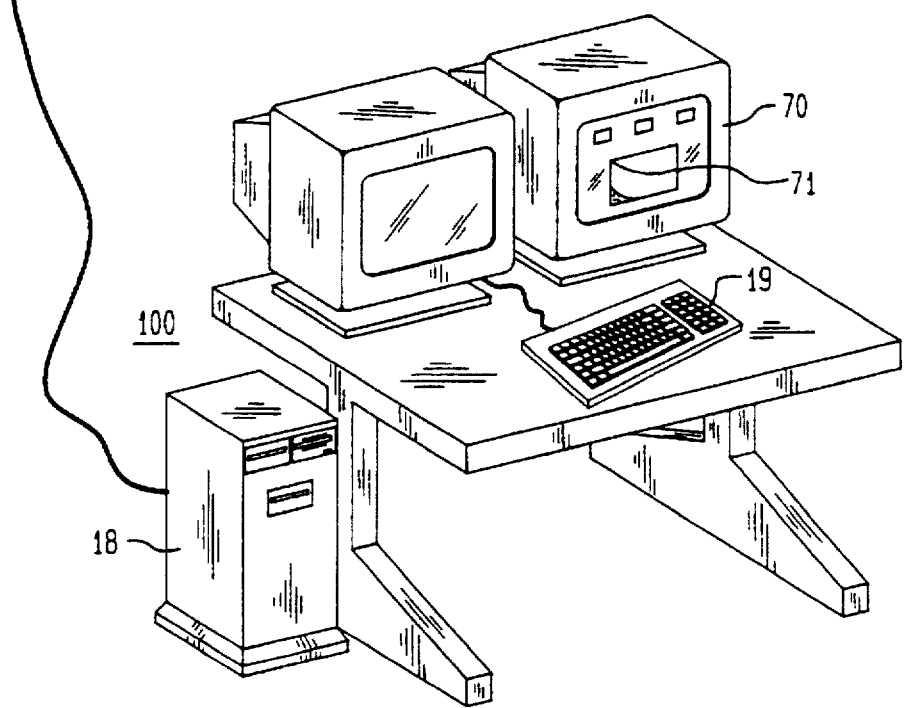

FIG. 1 shows a radiation treatment device 2 of common design. Radiation device 2 includes plates 4, a control unit in a housing 9, and a gantry 6. Plates 4 are fastened to a projection of gantry 6. Gantry 6 can be swiveled around a horizontal axis of rotation 8 during therapeutic treatment. To generate the high-powered radiation required for therapy, a linear accelerator is located within gantry 6. The axis of the radiation bundle emitted from the linear accelerator and gantry 6 is designated by 10. Electron, photon, or any other detectable radiation can be used for the therapy.

During treatment, the radiation beam is focused on a zone 12 of an object 13 (e.g., a patient who is to be treated, and who lies at the isocenter of the gantry rotation). The rotational axis 8 of gantry 6, the rotational axis 14 of the area to be treated, and the beam axis 10 all preferably intersect in the isocenter of zone 12. The construction of such a radiation treatment device is described in general in a brochure "Digital Systems for Radiation Oncology", Siemens Medical Laboratories, Inc. A91004-M2630-B358-01-4A00, September 1991.

The area of the patient that is irradiated is sometimes referred to as the "field". Plates 4 are substantially impervious to emitted radiation. They are mounted between the radiation source and the patient to delimit the radiation such that it more accurately irradiates the field. Areas of the body outside the field (e.g., healthy tissue) are therefore subjected to as little radiation as possible, and preferably to none at all. In the preferred embodiment of the invention, at least one of the plates is movable so that the distribution of radiation over the field need not be uniform (one region can be given a higher dose than another). Furthermore, the gantry can be rotated to allow different beam angles and radiation distributions without having to move the patient. The present invention can also be used with fixed-field devices (i.e., no movable plates), with constant radiation delivery rates, and with fixed-angle beams (i.e., no rotatable gantry).

Moreover, plates, although common, are not the only type of beam-shielding devices available. For example, most radiation devices contain some form of beam collimator, wedge, compensator, jaw and/or other aperture device. Thus, the aperture device itself can act as the beam-shielding device, and the various beam-shielding devices can be combined to limit the delivered radiation. The present invention can be used with any such arrangement. The invention can also be used in dynamic conformal treatments during which the gantry, collimator, jaws and multileaf collimators could all be in motion during the radiation distribution.

Radiation treatment device 2 also includes treatment unit 100 which is usually located apart from gantry 6 and treatment table 16. Preferably, the radiation treatment device 2 is located in a different room from treatment unit 100 to protect the therapist from radiation exposure. Treatment unit 100 includes an output device, such as a visual display unit or monitor 70, and a keyboard 19. Treatment unit 100 is routinely operated by a therapist who administers delivery of a radiation treatment as prescribed by an oncologist. The treatment unit includes a central processing unit (CPU) 18, whose function is described below. By utilizing keyboard 19, the therapist can program treatment unit 100, so that the prescribed radiation is delivered to the patient. The program can also be input via another input device such as a data storage device located within the central processing unit (CPU) 18 or through data transmission to CPU 18.

In the preferred embodiment, a portal imaging system 90 is attached to gantry 6. This portal imaging system includes a detector unit. This detector unit is capable of measuring the radiation exiting object 13. The amount of radiation exiting object 13 (i.e., the exit dose information) can be used to verify the radiation treatment. Thus, the detector unit within portal imaging system 90, is used to gather the patient's exit dose information. The delivered radiation dose is then reverse calculated by CPU 18. The delivered radiation dose is then compared to the planned delivery dose. If these dose amounts match, the prescription was executed as planned. If the amounts do not match, measures can be taken for correction (e.g., more or less radiation can be distributed at the following radiation treatment session(s)). Thus, radiation distribution can be either verified or corrected.

In the preferred embodiment of the present invention, the exit dose is displayed on the screen of monitor 70 in a display area 71 which can cover the entire screen. Various other data can also be displayed before, during and after treatment on monitor 70. Thus, display area 71 can cover a portion of the screen and can be designed as a window or as an icon. In addition to the measured delivered radiation, the prescribed radiation can also be shown on the screen. The display of the measured delivered radiation is preferably carried out in real time. Thus, at any time during treatment, the amount of delivered radiation can be verified. In addition, at the end of a treatment, the overall delivered radiation can be verified with the prescribed radiation. This can be initiated automatically with a software program capable of detecting the end of a treatment, or this can be initiated manually by, for example, a therapist. Instead of or in addition to monitor 70, other output devices, such as a printer, can be utilized.

Figure 2:
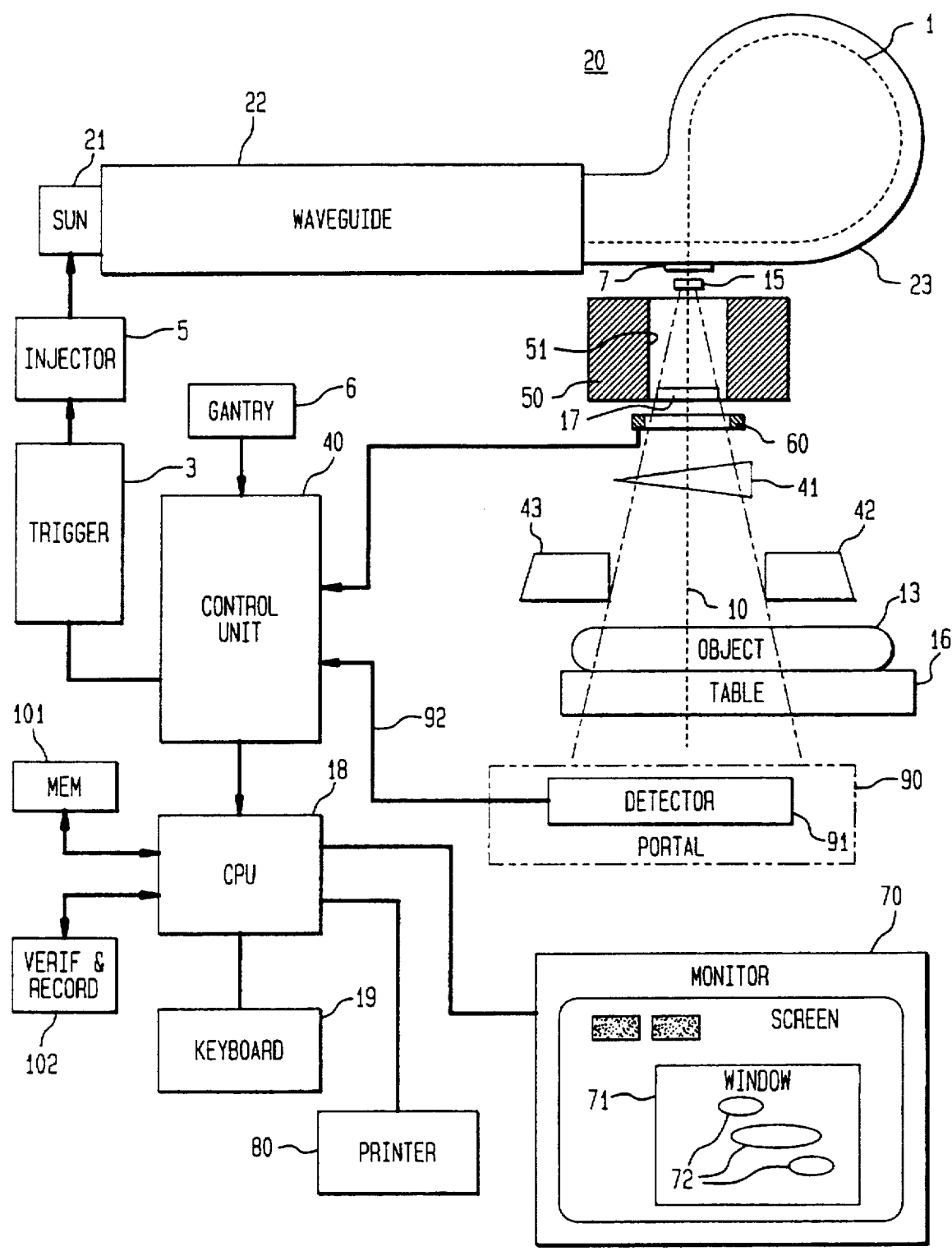
FIG. 2 is a block diagram illustrating portions of a processing unit, a control unit, and a beam generation system in the radiation treatment device of FIG. 1.

FIG. 2 shows portions of radiation treatment device 2 and portions of treatment unit 100 in more detail. An electron beam 1 (also referred to as a radiation beam) is generated in an electron accelerator 20. Accelerator 20 includes an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the radiation dose is ascertained. If the radiation beam is an x-ray beam, the scattering foils are replaced by a target. A wedge filter 41 and aperture plates 42 and 43 can be provided in the path of radiation beam 1 such that the radiation is focused on the area to be irradiated. As is described above, this is just one example of a beam-shielding arrangement that can be used in the present invention.

As stated above, a detector unit 91 is arranged beneath object 13 from the viewpoint of the beam source. In the preferred embodiment, detector unit 91 is located within portal imaging system 90. The amount of the radiation beam delivered to object 13 is measured by detector unit 91 such that radiation is sensed after it has passed through object 13.

FIG. 2 also shows various portions of treatment unit 100. Monitor 70 and keyboard 19 are connected to CPU 18. A printer 80 can also be provided to record information related to the treatment. CPU 18 is programmed to assist in the control of radiation treatment device 2. According to the instructions of the oncologist, the therapist programs CPU 18, so that it carries out the prescribed course(s) of radiation treatment. In window 71 on the screen of monitor 70, curves 72 indicate the prescribed delivery of the radiation treatment. A memory 101 along with a verification and recording system 102 can be connected to CPU 18.

A control unit 40 receives position information from gantry 6, and it receives information about radiation emission from measuring chamber 60. Detector unit 91 provides exit radiation signals 92 to control unit 40. These exit radiation signals 92 include information about the amount of radiation which has passed through object 13. CPU 18 processes signals received from control unit 40 and reverse calculates the incident beam for the distributed radiation. In the preferred embodiment, this incident beam is based on exit radiation signals 92 and on attenuation factors (e.g., the anatomical attenuation factors of object 13). The incident beam can also be based on exit radiation signals 92 alone. CPU 18 can then output a two dimensional or a three dimensional display of a radiation delivered dose map. This radiation map can be in the form of radiation dose curves 72 which provide a three dimensional display. The radiation map displays the calculated amount of radiation which has been distributed through object 13. Additionally, other curves, such as curves representing the planning system dose and/or icons related to a wedge function, can also be displayed on monitor 70.

Figure 3:
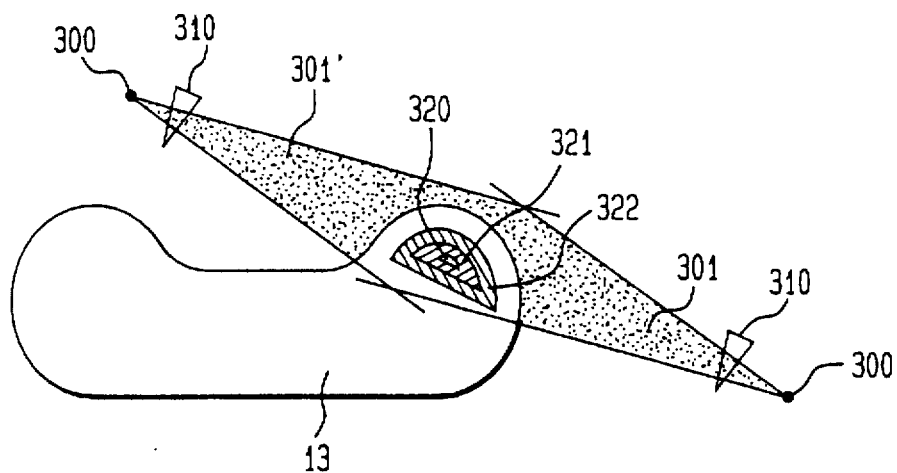
FIG. 3 illustrates a simplified planar view of a dose map for combined beams for a breast treatment.

FIG. 3 illustrates a simplified planar view of a dose map for combined beams for a breast treatment. In this example, object 13 is a female body which is irradiated by two radiation beams 301 and 301'. These radiation beams 301 and 301' are generated by the same beam source 300 which moves to different positions relative to object 13. Wedge filter 310 can be placed in the trajectory of beams 301 and 301'. The planning system predicts radiation dose levels 320–322 based on the combined two beam treatment.

Wedge filter 310 and the position of beam source 300 directly affect dose levels 320–322.

Figure 4:
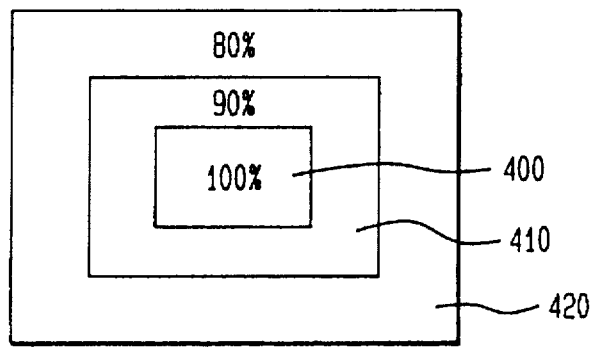
FIG. 4 shows a graph of a radiation dose from a beam's eye view of one beam sown in FIG. 3.

FIG. 4 shows a graph of a radiation dose from a beam's eye view of one beam shown in FIG. 3. Thus, FIG. 4 reveals the radiation dose distribution through object 13 according to this beam's eye view. The unsymmetrical distribution is due to wedge filter 310. In this example, 100% area 400 could correspond to radiation delivered dose 320 on object 13 (see FIG. 3). Similarly, 90% area 410 could correspond to radiation dose level 321, and 80% area 420 could correspond to radiation dose level 322.

Figure 5:
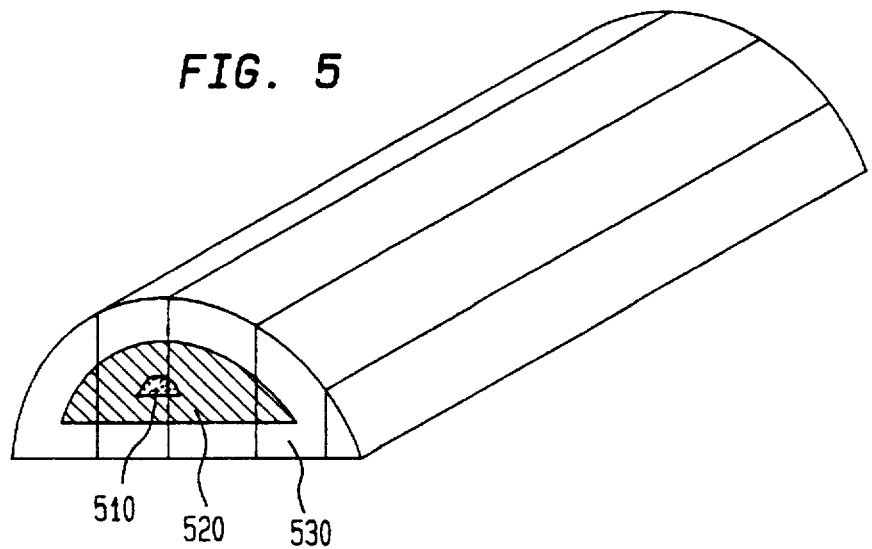
FIG. 5 shows a three dimensional radiation dose distribution.

FIG. 5 is a three dimensional view of the radiation dose distribution for the treatment shown in FIG. 3. This view includes the radiation distribution from both radiation beams 301 and 301'. In this example, area 510 corresponds to radiation dose level 320 (see FIG. 3), area 520 corresponds to dose level 321, and area 530 corresponds to dose level 322.

Figure 6:
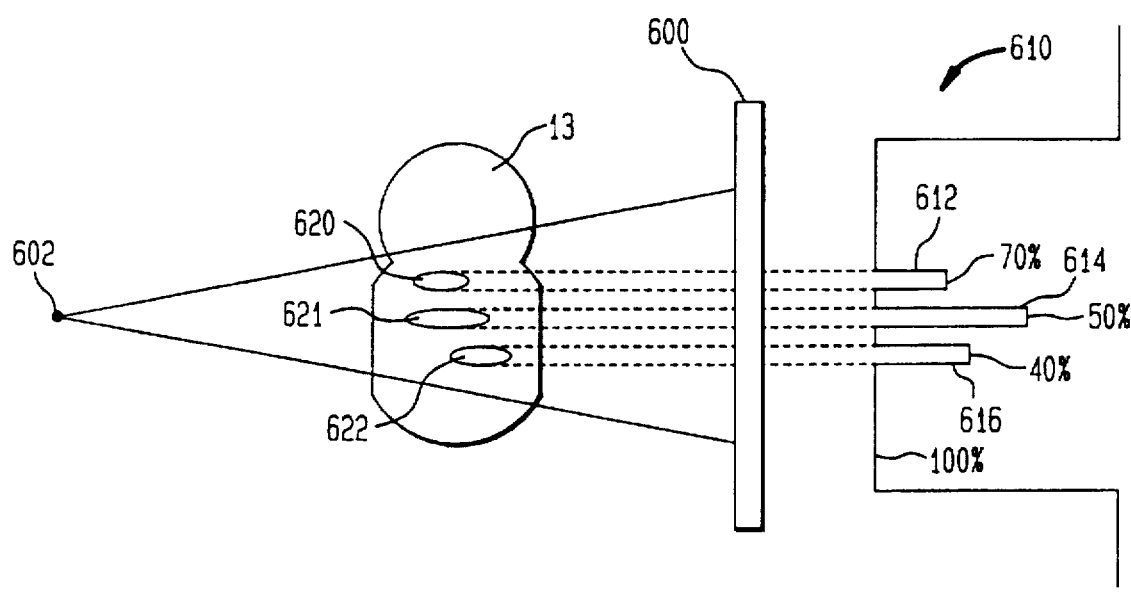
FIG. 6 illustrates the exit dose concept for radiation dose distribution.

FIG. 6 illustrates the exit dose concept for radiation dose distribution. The exit dose is collected by detector 600 which in this embodiment is part of portal imaging system 90. The control unit does a reverse calculation to determine the incident beam from radiation source 602. Again, the measured exit dose values and predetermined anatomical attenuation factors are used in this reverse calculation. A delivered radiation map 610 can then be generated. This delivered radiation map 610 can be generated real-time. As shown in FIG. 6, anatomical structures 620–622 in object 13 absorb between 30 and 60% of the delivered radiation. For example, anatomical structure 620 absorbed 30% of the delivered radiation. This is reflected in the corresponding 70% on section 612 of radiation map 610. Similarly, anatomical structure 621 absorbed 50% of the delivered radiation as shown in the corresponding 50% on section 614 of map 610, and anatomical structure 622 absorbed 60% as shown in the corresponding 40% on section 616 of map 610. Object 13 can contain one or more anatomical structures. The dose requirements from the planning system along with the measured exit dose values are used to verify the amount of radiation delivered to object 13.

Figure 7:
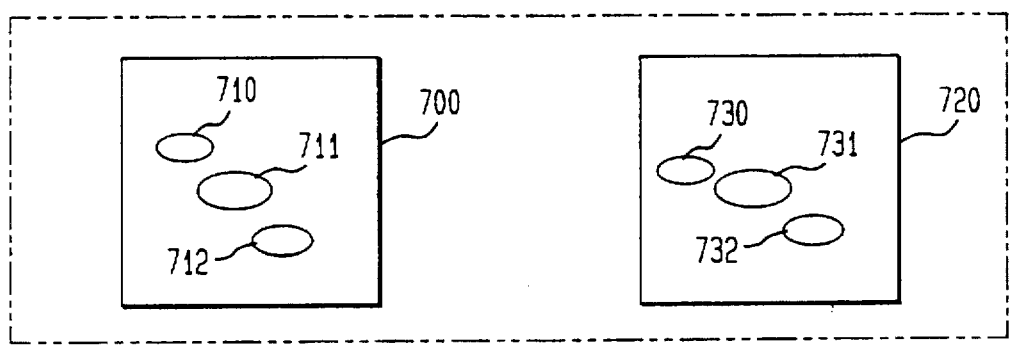
FIG. 7 shows an example of a graph of a radiation delivered dose map and a planning system radiation dose map.

FIG. 7 shows an example of a graph of a radiation map and a planning system radiation dose map. By using radiation map 610, CPU 18 can generate an exit dose map 700 which shows radiation dose curves 710–712. These radiation dose curves 710–712 represent the radiation distributed through object 13. In the preferred embodiment, radiation dose curves 710–712 correspond to sections 612, 614, 616 of radiation map 610, respectively. This exit dose map 700 can be displayed on the screen of monitor 70. Additionally, a planned radiation dose map 720 generated from the planning system can be displayed on the screen. Planned dose curves 730–732 represent the amount of radiation which should have been delivered to anatomical structures 620–622, respectively. If both exit dose map 700 and planned dose map 720 are displayed on the screen of monitor 70, a user can quickly, visually compare the calculated/derived radiation curves 710–712 with the planned dose curves 730–732. Thus, the therapist can quickly verify that the correct amount of radiation was delivered to the patient.

Figure 8A:
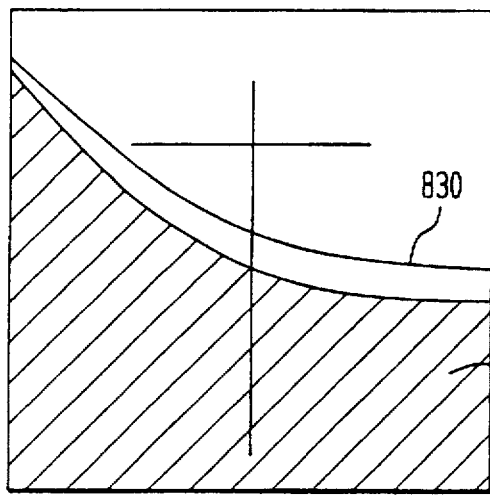
FIG. 8a shows an example of icons related to the delivered radiation and the prescribed radiation dose.

The parent patent application to the present invention, U.S. patent application Ser. No. 08/504,722, describes an example of how to display the accumulated dose delivered to an area to be irradiated. As shown in FIG. 8a, the radiation delivered can be displayed in window 810 on graph 820. Graph 820 is in the shape of a curve because a wedge was utilized during the radiation treatment. The amount of delivered radiation can also be updated throughout the radiation treatment process. Thus, when updates occur, graph 820 is modified accordingly. Also, a prescribed dose profile 830 may simultaneously be displayed, so that the user can compare the accumulated dose, as shown in graph 820, with prescribed dose profile 830. Again, the user can visually compare the prescribed amount of radiation to the delivered/derived amount of radiation. Moreover, if delivered radiation graph 820 extends past prescribed dose profile 830, an alarm can be given to the user and/or the radiation treatment can be automatically stopped. The alarm and the automatic turn off can be accomplished with a software program which monitors graphs 820 and 830. The alarm can be visual, audio or both.

Figure 8B:
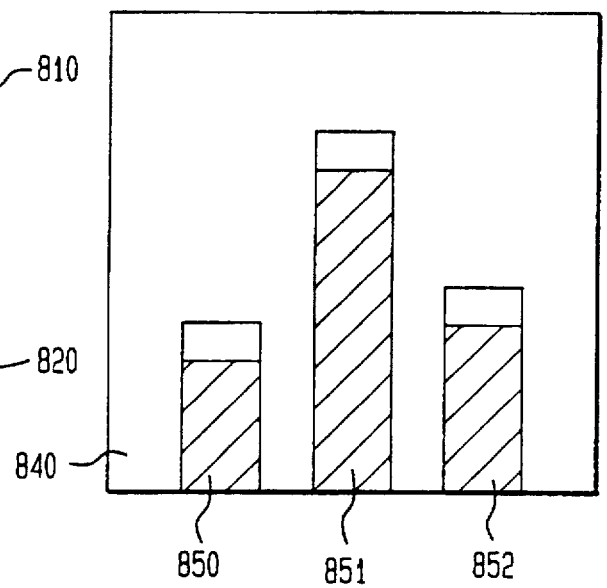
FIG. 8b shows an example of icons related to the exit radiation dose.

Additionally, as shown in FIG. 8b, the exit dose information which is gathered according to the present invention can be displayed on the screen as graph 840. Both graphs can be displayed as icons, graphs, charts (e.g., bar charts, pie charts, etc.) or the like, and they can be placed in any areas on the screen. FIG. 8b utilizes a bar graph. Bars 850–852 can represent both the planned radiation dose and the delivered/derived radiation dose for various anatomical structures. For example, bar 850 could correspond to anatomical structure 620 in FIG. 6. In this example, the bottom portion of bar represents the amount of radiation actually delivered to anatomical structure 620, and the top portion of bar 850 represents the remaining amount of radiation which needs to be delivered to anatomical structure 620. Thus, bar 850, in its entirety, represents the amount of the planned radiation dose. Again, an alarm or automatic shut off can be used if the top of bar 850 is exceeded.

Figure 9:
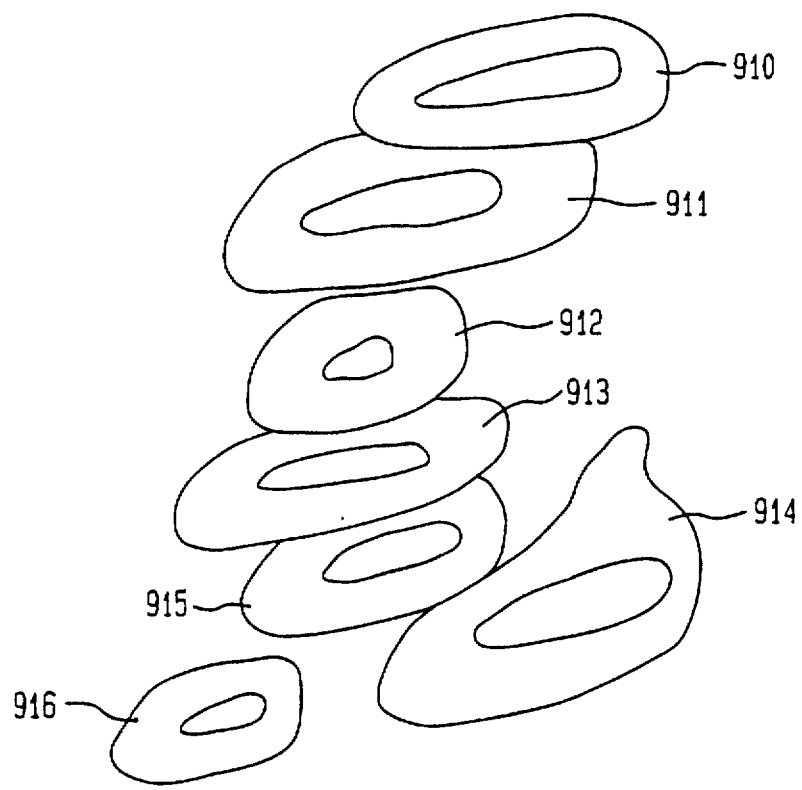
FIG. 9 shows an example of a three dimensional icon for the radiation delivered dose map.

As shown in FIG. 9, predicted radiation dose curves 910–916 can be displayed as a three dimensional graph 900. This graph 900 represents a treatment in which multiple treated areas (seven in this example) within one object are summarized. As the radiation treatment occurs, the radiation dose curves 910–916 fill up as shown. For example, the amount of delivered radiation can be represented by the inner circles within curves 910–916, and the amount of planned radiation can be represented by the outer circles which define curves 910–916. These displays verify treatment and give the user confidence that the patient is being treated correctly. Again, an alarm and/or automatic shut off can be used if the inner circle expands beyond the curves 910–916. Any other type of two-dimensional or three-dimensional display can be used in a similar manner.

What is claimed is:

1. A system for verifying radiation delivered to an object, the system comprising:

a radiation source with an output beam directed to the object;

detector means for sensing radiation output from the output beam and for generating exit radiation signals, the detector means sensing the output radiation beneath the object; and processing means for calculating the radiation delivered to the object, the processing means using the exit radiation signals from the detector means for the calculation.

2. The system for verifying radiation delivered to an object of claim 1, wherein the processing means is capable of generating a delivered radiation map, the delivered radiation map being reverse calculated, the reverse calculation being based on the exit radiation signals from the detector means and attenuation factors of the object.

3. The system for verifying radiation delivered to an object of claim 2, further comprising output means for outputting the delivered radiation map during delivery of the radiation.

4. The system for verifying radiation delivered to an object of claim 1, wherein the detector means is located in a portal imaging system arranged beneath the object.

5. The system for verifying radiation delivered to an object of claim 2, wherein the processing means displays the delivered radiation map in a two dimensional manner.

6. The system for verifying radiation delivered to an object of claim 1, wherein the processing means simultaneously outputs radiation dose curves of a planned radiation.

7. The system for verifying radiation delivered to an object of claim 6, wherein the radiation dose curves for the planned radiation are filled out as radiation is delivered to the object.

8. The system for verifying radiation delivered to an object of claim 3, wherein the output means is at least one of a monitor and a printer.

9. A method for verifying radiation delivered to an object, the object containing a field to be irradiated, the method comprising the steps of:

generating an initial output beam of radiation from a radiation source, the initial output beam being directed toward the field on the object;

sensing exit radiation from the initial output beam directed towards the field, the sensing occurring after the radiation passes through the object; and calculating the derived output beam, the derived output beam being at least in part based on the sensed exit radiation.

10. The method for verifying radiation delivered to an object of claim 9, further comprising the step of generating exit radiation signals, the exit radiation signals corresponding to the sensed exit radiation.

11. The method for verifying radiation delivered to an object of claim 10, wherein the calculating of the derived output beam is at least in part based on the exit radiation signals and attenuation factors of the object.

12. The method for verifying radiation delivered to an object of claim 9, further comprising the step of outputting a radiation map, the radiation map including information from at least one of the derived output beam and a planned radiation dose.

13. The method for verifying radiation delivered to an object of claim 12, further comprising the step of displaying the radiation map.

14. The method for verifying radiation delivered to an object of claim 12, wherein radiation dose curves from the planned radiation dose are filled out as the initial output radiation is delivered.

15. The method for verifying radiation delivered to an object of claim 12, further comprising the step of displaying the radiation map on at least one of a monitor and a printer, the displaying occurring when radiation is being delivered to the object.

* * * * *